United States Patent
Corech

(10) Patent No.: US 6,567,159 B1
(45) Date of Patent: May 20, 2003

(54) SYSTEM FOR RECOGNIZING A GAMING CHIP AND METHOD OF USE

(75) Inventor: Hertsel Corech, Los Angeles, CA (US)

(73) Assignee: Gaming Analysis, Inc., Bell Gardens, CA (US)

(*) Notice: Subject to any disclaimer, the term of this patent is extended or adjusted under 35 U.S.C. 154(b) by 406 days.

(21) Appl. No.: 09/593,936

(22) Filed: Jun. 15, 2000

Related U.S. Application Data

(60) Provisional application No. 60/159,224, filed on Oct. 13, 1999.

(51) Int. Cl.[7] .......................... G06K 9/74; G01N 21/86
(52) U.S. Cl. ........................ 356/71; 250/559.4
(58) Field of Search .................. 356/71; 40/27.5; 453/58; 273/126 R, 353, 290, 291, 305; 473/588; 209/580; 156/406, 407, 408; 250/226, 221, 222.1, 559.4

(56) References Cited

U.S. PATENT DOCUMENTS

| | | | | |
|---|---|---|---|---|
| 3,679,314 A | * | 7/1972 | Mustert | 250/226 |
| 3,867,039 A | * | 2/1975 | Nelson | 209/582 |
| 3,910,701 A | * | 10/1975 | Henderson et al. | 250/226 |
| 4,026,309 A | * | 5/1977 | Howard | 194/214 |
| 4,157,139 A | * | 6/1979 | Bjork | 198/397.05 |
| 4,259,020 A | * | 3/1981 | Babb | 356/243.5 |
| 4,379,233 A | * | 4/1983 | Rosenthal | 250/223 R |
| 4,518,258 A | * | 5/1985 | Broersma | 356/223 |
| 4,652,136 A | * | 3/1987 | Harjunmaa | 356/408 |
| 4,878,756 A | * | 11/1989 | Stauffer | 356/406 |
| 4,917,500 A | * | 4/1990 | Lugos | 250/226 |
| 5,021,645 A | * | 6/1991 | Satula et al. | 209/580 |
| 5,166,985 A | * | 11/1992 | Takagi et al. | 348/128 |
| 5,229,841 A | * | 7/1993 | Taranowski et al. | 356/406 |
| 5,283,422 A | * | 2/1994 | Storch et al. | 235/375 |
| 5,531,331 A | * | 7/1996 | Barnett | 198/397.07 |
| 5,608,207 A | * | 3/1997 | Allen et al. | 250/214 AG |
| 5,757,876 A | * | 5/1998 | Dam et al. | 377/14 |
| 5,781,647 A | * | 7/1998 | Fishbine et al. | 235/375 |
| 5,799,105 A | * | 8/1998 | Tao | 348/187 |
| 5,929,999 A | * | 7/1999 | Butterworth | 250/226 |
| 5,933,244 A | * | 8/1999 | Kiritchenko | 209/580 |
| 5,977,537 A | * | 11/1999 | Hsieh | 250/216 |
| 6,075,217 A | * | 6/2000 | Kiritchenko | 209/582 |
| 6,124,936 A | * | 9/2000 | Okamoto | 250/226 |
| 6,147,761 A | * | 11/2000 | Walowit et al. | 356/328 |
| 6,272,440 B1 | * | 8/2001 | Shakespeare et al. | 250/559.04 |
| 6,384,409 B1 | * | 5/2002 | Libbey, III et al. | 235/468 |

* cited by examiner

Primary Examiner—Zandra V. Smith
Assistant Examiner—Gordon J Stock
(74) Attorney, Agent, or Firm—Timothy Thut Tyson; Ted Masters; Freilich, Hornbaker & Rosen

(57) ABSTRACT

A system (20) for recognizing gaming chips (500) includes pairs of light emitting devices $P_1$ through $P_n$, each pair emitting light (28) of a different color. The light (28) is reflected off of the surface (502) of the gaming chip (500), is sensed by a light detector (32), digitized by an analog to digital converter (33), and compared with stored intensity profiles for various denomination gaming chips (500). When a match is obtained, system (20) issues a signal indicating the color, and thus denomination, of the gaming chip (500). An energizing circuit (26) produces a constant current to ensure a constant light intensity level. An automatic adjustment circuit (40) changes the constant current to accommodate for factors such as component aging. Adjustment circuit (40) is controlled by a calibration feature wherein light (28) is reflected off of a calibration surface (42) while system (20) is in use.

4 Claims, 5 Drawing Sheets

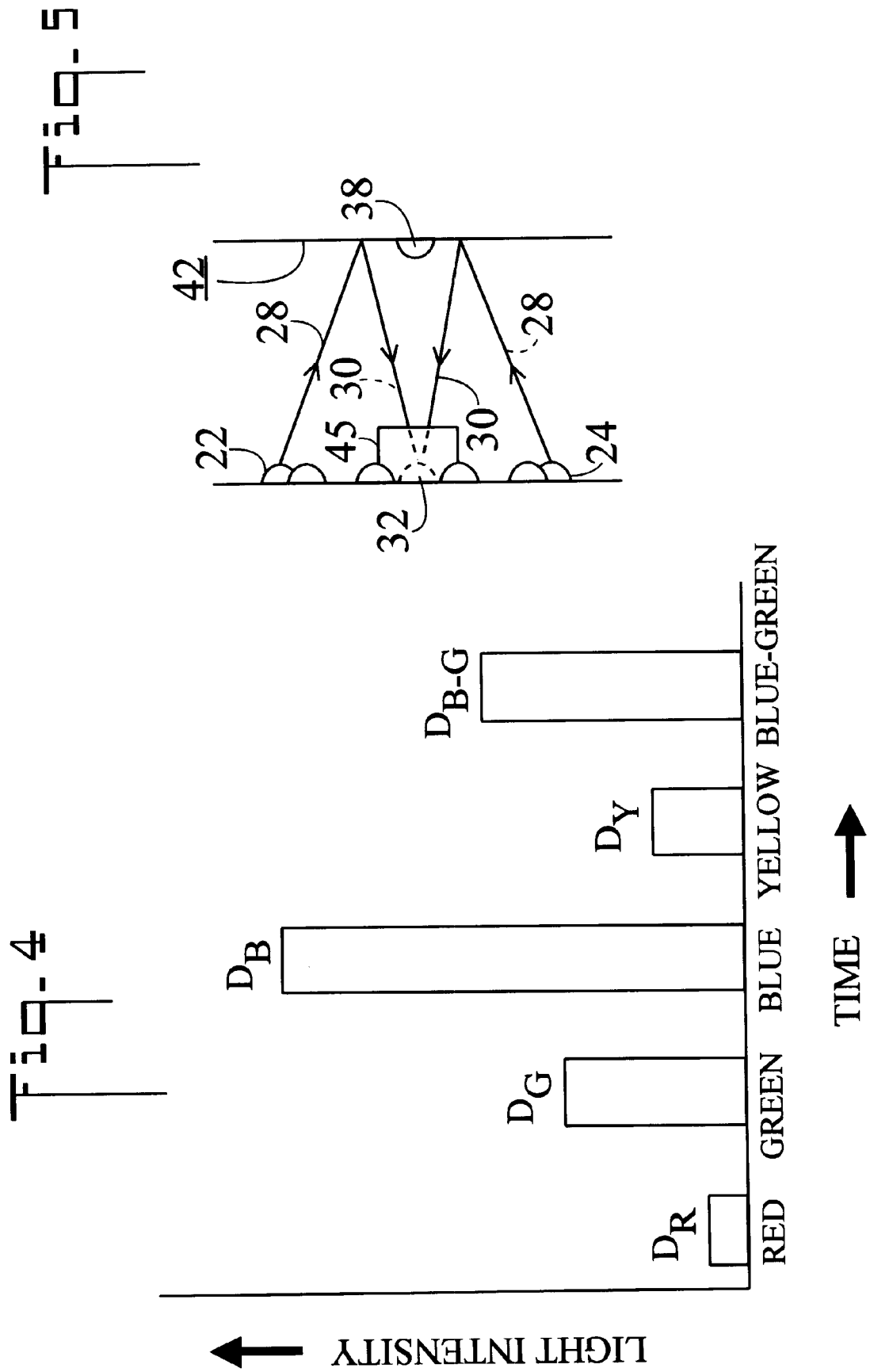

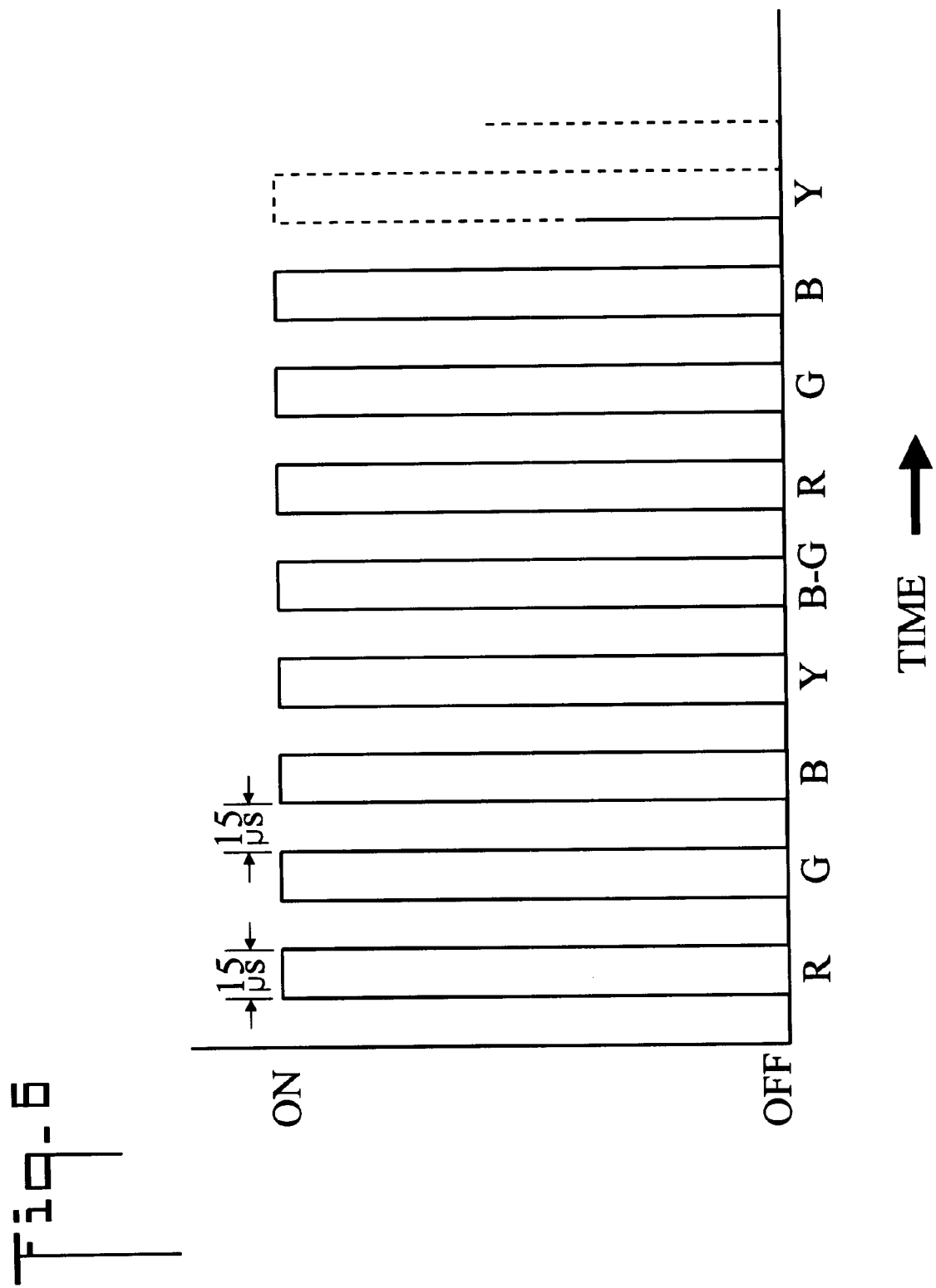

SYSTEM FOR RECOGNIZING A GAMING CHIP AND METHOD OF USE

CROSS-REFERENCE TO RELATED APPLICATION

This application claims the filing benefit under 35 U.S.C. §119(e) of U.S. Provisional Application No. 60/159,224, filed Oct. 13, 1999, which is included herein by reference.

TECHNICAL FIELD

The present invention generally pertains to the gaming industry, and in particular to system for recognizing the color and therefore monetary denomination of a gaming chip.

BACKGROUND ART

Devices for sorting, counting, and determining the value of gaming chips are well known in the art. For example:

U.S. Pat. No. 4,026,309 shows a chip counter for use in gaming applications and the like. The counter includes a slitted tray having a trough for receiving chips. The chips have a reflective strip around their periphery. Different strips emit different wave lengths to denote chip denomination. The system uses various filters in the color determination process.

U.S. Pat. No. 4,157,139 illustrates an system for sorting and/or handling disc-like members such as casino chips. The invention includes a gravity feed feature. The invention also sorts the chips by color, using photoelectric or other means.

U.S. Pat. No. 5,042,810 defines a roulette system which discloses the sorting of casino chips by color. The patent does not describe how the color sorting is performed.

U.S. Pat. No. 5,103,081 discloses an system and method for reading encoded data on circular objects such as gaming chips. A circular bar code is used to determine the denomination of the chips. The chips drop through a machine during the reading process.

U.S. Pat. No. 5,361,885 includes an anti-counterfeiting device for gaming chips. Light-receiving faces are arrayed about the circumference of the chip. The number of faces determines the value of the chip.

U.S. Pat. No. 5,531,331 comprises an system for sorting gaming chips by color. The use of photodetectors to effect color differentiation is disclosed.

U.S. Pat. No. 5,757,876 consists of an object counter and identification system. The system counts and identifies chips by color for the purpose of (1) informing the gaming establishment if the house is winning or losing, (2) the amount of money being wagered, (3) the efficiency of the dealer, etc. The system communicates with a computer which processes the counting information received from the sensors.

U.S. Pat. No. 5,781,647 shows a gambling chip recognition system. The system uses a video camera which determines the color, and thus value, by looking at the edge of the chip. Data from the color sensor is provided to a computer system where it is processed into information useful to the operators of the casino.

U.S. Pat. No. 5,788,574 describes a method and system for playing a betting game including a side bet. The system includes a microprocessor cooperating with a sensor which identifies the denomination of the chips by color. The system utilizes three light emitting diodes and one light sensitive diode to identify the chip color. The light emitting diodes emit yellow, green, red or colored light.

U.S. Pat. No. 5,919,090 defines an system and method for data gathering in games of chance. The invention does include chip sensors which are connected to a computer data processing system.

U.S. Pat. No. 5,933,244 depicts a method of article identification through color determination. The method includes a color sensor and an article (chip) being moved relative to one another and a plurality of sensor readings are taken and then integrated to arrive at the color. The chip falls past the color sensor.

U.K. Patent 2,061,490 discloses a system for identifying and sorting gambling chips by color. It includes a plurality of photo sells, each of which is tuned to respond to the color of a particular value chip. After the correct color is sensed, the chip is mechanically routed to an appropriate stack of similar chips.

In a related technology, U.S. Pat. No. 5,335,293 illustrates an automated quality inspection station for evaluating color component characteristics of a product. The station includes a color video camera, for capturing video frames of product images, and a control system for analyzing those video frames. The control system is programmed to perform a reference calibration and then a sample calibration. During the reference calibration an operator identifies component type areas from a displayed reference frame of a typical product assortment. The control system calculates color value density curves from the identified areas. The density curves are then calibrated to each other by scaling each of the density curves by a scaling factor.

In the gaming industry it is desirable for casino management to have instantaneous information for all tables as to how play is progressing, the amount of money being wagered, the efficiency of a particular dealer, and other related information. It is to that purpose that the present invention is directed.

DISCLOSURE OF INVENTION

The present invention is directed to a system for recognizing the color, and therefore the denomination of gaming chips. In a preferred embodiment the present invention employs a plurality of pairs of light emitting devices, each pair emitting a different color light. The light emitting devices illuminate the entire surface of the gaming chip and therefore the light reflected from the surface of the gaming chip provides a composite average of all of the colors of the chip, regardless of how many colors there are, or how the colors are distributed upon the surface of the gaming chip. The present invention measures the total light reflected off of the chip's surface, and compares the measured light with standard light intensity profiles for each denomination chip. When a match is achieved, the system produces an indication of the chip's monetary denomination. If the measured light does not match any of the standard light profiles, the chip is categorized as an unauthorized or counterfeit chip, and an appropriate message generated.

A computer is utilized to collect, control, and process the gaming chip information. The computer develops an extensive computer database and graphic user interface which is useful in casino management. For example, all of the gaming chip information collected by the system many be counted, totaled, date-stamped, time-stamped, associated with a particular gaming table, associated with a particular dealer, and displayed in various useful formats.

In accordance with a preferred embodiment of the invention, a system for recognizing a gaming chip includes a pair of spaced apart light emitting devices, each light emitting device of the pair emitting light of the same predetermined color. An energizing circuit simultaneously energizes the pair of light emitting devices so that for a brief period of time they illuminate the surface of the gaming chip. Light reflected from the surface of the gaming chip is sensed by a light detector.

In accordance with another preferred embodiment of the invention, a plurality of pairs of light emitting devices are utilized, each pair emitting light of a different color. The pairs are energized in rapid sequential order many times in order to obtain a very accurate average measurement of the reflected light.

In accordance with an important feature of the invention, the gaming chip is dropped into a slot in the top of a gaming table and gravity causes the chip to fall past the light emitting devices and light detector.

In accordance with another important aspect of the invention, a detector circuit detects the presence of a gaming chip. The detector circuit then activates the energizing circuits associated with each pair of light emitting devices.

In accordance with another important feature of the invention, the energizing circuit delivers a constant current to each light emitting device so that the intensity of the light emitted by the light emitting device is also constant. An adjustment circuit is provided for automatically changing the value of the constant current to compensate for changes in the light emitting properties of the light emitting device. The adjustment circuit includes a micro-controller/controlled digital potentiometer.

In accordance with an important aspect of the invention, a hood surrounds the light detector to prevent light from the light emitting device from directly striking the light detector.

In accordance with an important feature of the invention, periodically when a gaming chip is not present, the light emitting devices are energized, the light striking a calibration surface. The amount of light reflected from the calibration surface is utilized to trigger the adjustment circuit which in turn automatically adjusts the level of constant current, and thereby the intensity of emitted light, in order to produce a desired intensity of reflected light.

Other features and advantages of the present invention will become apparent from the following detailed description, taken in conjunction with the accompanying drawings, which illustrate, by way of example, the principles of the invention.

BRIEF DESCRIPTION OF DRAWINGS

FIG. 4 is a graph of reflected light intensity from a particular gaming chip;

FIG. 5 is a side elevation view of the plurality of light emitting devices and the light detector, when a gaming chip is not present;

FIG. 6 is a graph of showing the sequential and repeated energization of the light emitting devices; and, FIG. 7 is a block diagram of a second embodiment of the system showing a different method of calibrating the light emitting devices.

MODES FOR CARRYING OUT THE INVENTION

Figure 1:
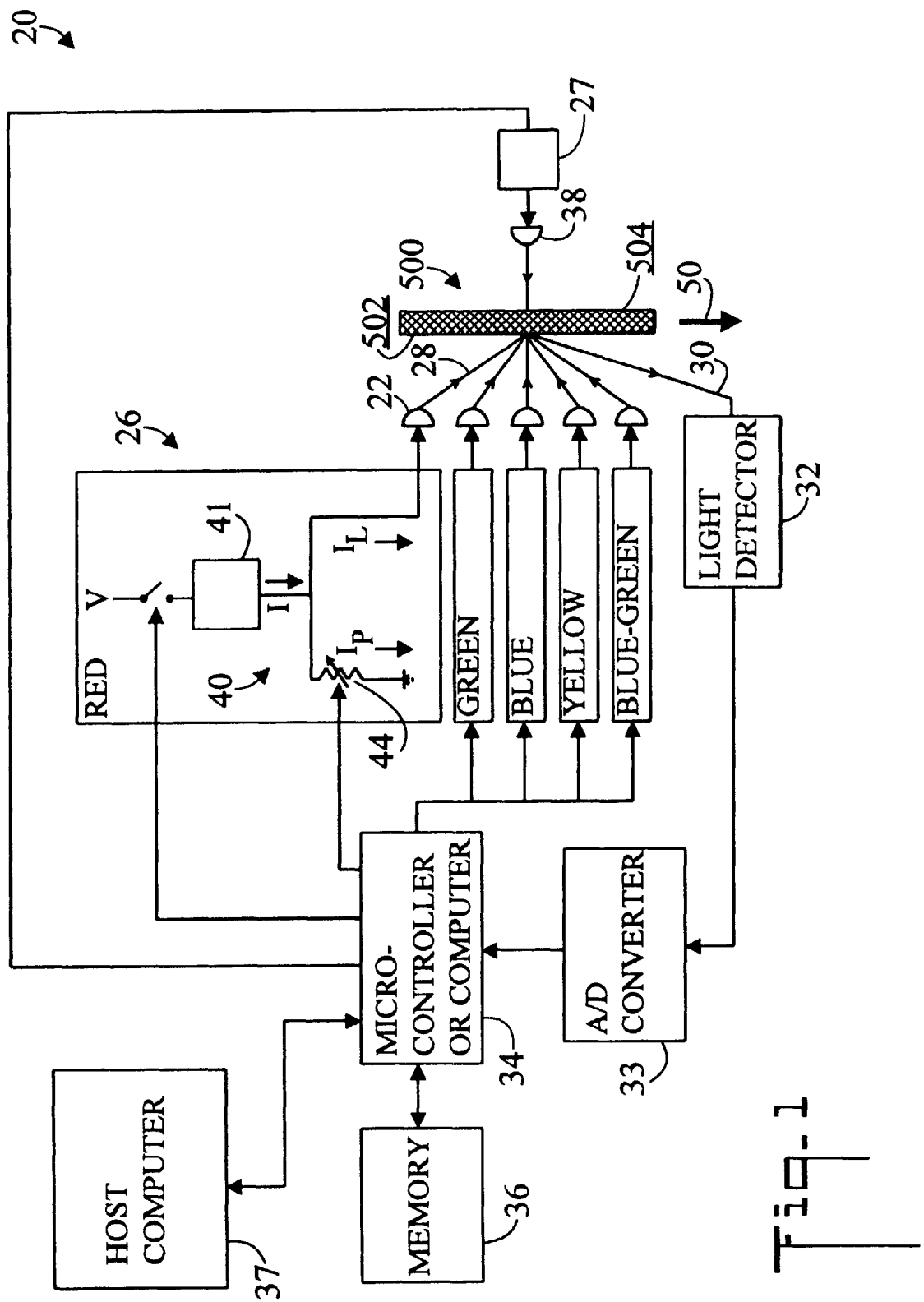
FIG. 1 is a block diagram of system for recognizing a gaming chip in accordance with the present invention.

Referring initially to FIG. 1, there is illustrated a block diagram of a system for recognizing a gaming chip in accordance with the present invention, generally designated as 20. The gaming chip 500 is typically disk-shaped having usually identical front and back substantially planar surfaces 502 and 504 respectively. It is noted however that the present invention can operate successfully even if the front 502 and back 504 surfaces are of different colors or patterns. System 20 includes a first pair $P_1$ of light emitting devices including a first light emitting device 22 which when energized emits light of a first predetermined color, and a second light emitting device 24, spaced apart for first light emitting device 22, when energized the second light emitting device emitting light of the same first predetermined color, for example red (refer also to FIGS. 2 and 3). An energizing circuit 26 simultaneously energizes the first pair $P_1$ of light emitting devices for a short period of time. The energizing circuit 26 for the red pair is depicted in the figure, however it may be appreciated that the other colors have an identical energizing circuit 26. When so energized, light 28 from the first pair $P_1$ of light emitting devices strikes surface 502 of the gaming chip 500, and the surface 502 of the gaming chip 500 emits reflected light 30. The reflected light 30 is received and sensed or measured by a light detector 32. In a preferred embodiment, light emitting devices 22 and 24 are light emitting diodes (LEDs), and light detector 32 is a photodiode, however it may be appreciated that other light emitting devices and sensors could also be employed.

Light detector 32 senses reflected light 30 and sends a signal proportional to the intensity of reflected light 30 to analog to digital (A/D) converter 33 where the signal is converted to a digital value. The digital value is then routed to micro-controller 34 for comparison with a plurality of pre-established intensity profiles which have been previously stored in memory 36, each pre-established intensity profile representing a baseline digital value(s) for a particular color gaming chip 500. The sensed digital value will match one and only one intensity profile, thereby determining the color and therefore the denomination of the gaming chip 500. Gaming chip 500 information is routed from micro-controller 34 to a personal host computer 37 where summary information useful to casino management is compiled and displayed.

In another embodiment of the present invention, micro-controller 34 and memory 36 are eliminated, and their functions are performed by computer, such as a PC.

Figure 3:
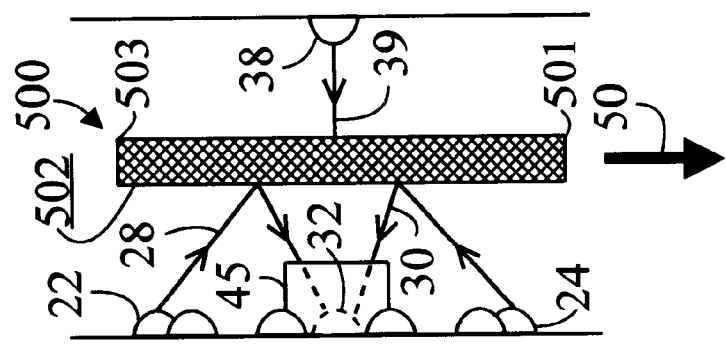
FIG. 3 is a side elevation view of the plurality of light emitting devices, the light detector, and the gaming chip.
Figure 2:
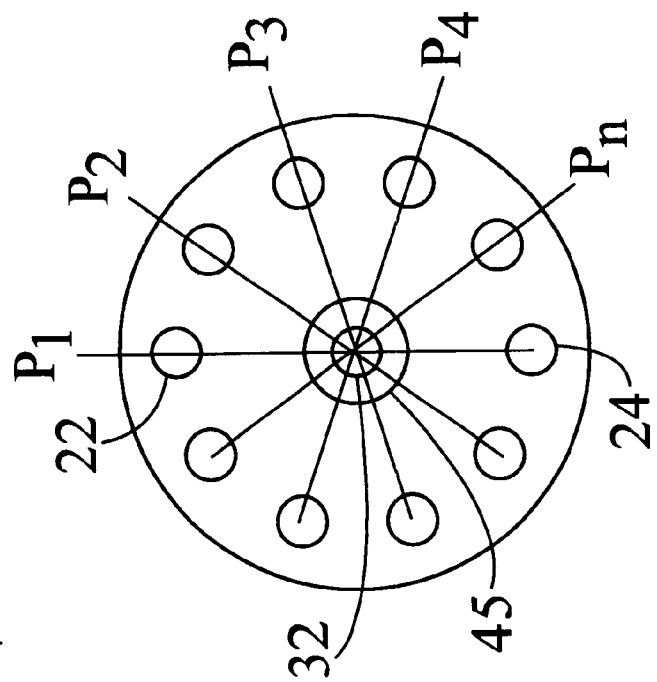
FIG. 2 is a front elevation view of a plurality of light emitting devices and a light detector.

Referring also to FIGS. 2 and 3, there are illustrated respectively front and side elevation views of a plurality of light emitting devices, light detector 32, and gaming chip 500. In a preferred embodiment of the present invention, a plurality of pairs of light emitting devices $P_1$ through $P_n$ are provided, each pair of light emitting devices emitting light of a different color. For example, pair $P_1$ might emit red light, $P_2$ might emit green light, pair $P_3$ might emit blue light, pair $P_4$ might emit yellow light, and pair $P_5$ might emit blue-green light. It may be appreciated that other colors and combinations of colors could also be utilized. In operation, the pairs of light emitting devices $P_1$ through $P_n$ are energized in rapid sequential order, the light detector 32 sensing a light intensity value as each pair is energized. That is, devices $P_1$ are turned ON and then OFF, then devices $P_2$ are turned on and off, etc.(refer to FIG. 6). In a preferred embodiment, the cycle is repeated so that each pair of light emitting devices is energized a plurality of times, for example 100 or more times for each gaming chip 500 to be recognized. The many readings are then averaged to produce a more accurate intensity level.

It is also noted that by using two spaced apart light emitting devices 22 and 24, the surface 502 of gaming chip 500 is more evenly illuminated, thereby ensuring a more accurate light intensity reading. It is also noted that the more light emitting pairs, the greater the accuracy in recognizing gaming chips 500. This is because there are more comparative light intensity values to compare, one for each pair. It is further noted that instead of pairs, three, four, or more light emitting devices could also be employed to further even out the illumination.

It is noted that light emitting devices $P_1$ through $P_n$ and light detector 32 may be either moving or stationary with respect to gaming chip 500. In a preferred embodiment, gaming chip 500 is dropped into a slot in a gaming table and gravity causes the gaming chip 500 to fall in direction 50 in front of light emitting devices $P_1$ through $P_n$ and light detector 32.

System 20 further includes a detector circuit for detecting the presence of a gaming chip 500. In a preferred embodiment, the detector circuit includes a position light emitting device 38 (refer to FIG. 3) which directs light beam 39 toward light detector 32. Energizing circuit 27 energizes position light emitting device 38. When a gaming chip 500 comes between position light emitting device 38 and light detector 32, light beam 39 is blocked and a signal is sent to micro-controller 34 which in turn activates energizing circuits 26 causing light emitting device pairs $P_1$ through $P_n$ to sequentially illuminate gaming chip 500.

In a preferred embodiment of the present invention, energizing circuit 26 delivers a constant current $I_L$ to light emitting device 22, as well as to all other light emitting devices. A constant current source 41 supplies a constant current I, a portion of which, $I_L$, is delivered to light emitting device 22. Since light intensity is directly proportional to the drive current, by producing a constant current the intensity of light emitting devices $P_1$ through $P_n$ remains constant, and therefore the reflected light 30 from gaming chip 500 may be accurately compared with the light intensity profiles stored in memory 36. This is important since variations in the level of light could falsely interpreted by micro-controller 34 as variations in the corresponding color of gaming chip 500. However, as light emitting devices $P_1$ through $P_n$ age they generally emit less light, which would adversely affect the comparison. To solve this problem, an automatic adjustment circuit 40 changes (typically increases) the constant current $I_L$ to accommodate for variations in reflected light 30. The adjustment circuit 40 includes a micro-controller 34 controlled digital potentiometer 44. As digital potentiometer 44 changes value, its current $I_P$ will decrease or increase, and by Kirchoff's Law, correspondingly increase or decrease constant current $I_L (I=I_L+I_P)$.

In terms of physical construction, pairs of light emitting devices $P_1$ through $P_n$ are arranged in a circular pattern on a printed circuit board, the diameter of the circle being about the diameter of the gaming chip 500 (about 1.75 inches). Light detector 32 is placed at the center of the circle, also on the printed circuit board. A pattern other than circular could also be utilized, so long as the gaming chip 500 is evenly illuminated. Position light emitting device 38 is mounted away from light detector 32, at the opposite side of a chute, in such a way that its light can be seen by light detector 32, but will be interrupted (blocked) when a gaming chip 500 falls through the slot and down the chute.

In a preferred embodiment, light detector 32 has a hood 45 to prevent light from light emitting devices $P_1$ through $P_n$ from directly striking light detector 32. That is, the light received by light detector 32 is only reflected light from the surface 502 of gaming chip 500, or from a calibration surface 42 (see below) if no gaming chip 500 is present.

Referring to FIG. 3, another unique feature of system 20 may be found in the way the reflected light 30 from gaming chip 500 is processed. In a preferred embodiment the at least one light emitting device is energized a plurality of times when gaming chip 500 interrupts light 39 from position light emitting device 38 as it passes in front of light detector 32. As gaming chip 500 falls past light detector 32, first end 501 initially breaks light beam 39. This starts the energization of the light emitting device, which concludes when opposite second end 503 clears light beam 39. During this period of energization, the light emitting device is energized a plurality of times (typically 100s of times or more). Each time of energization, light detector 32 receives reflected light 30 from the light emitting device, the light detector 32 provides an output signal proportional to intensity of the reflected light 30. The plurality of output signals corresponding to the plurality of energizations is routed to analog to digital 33 converter (refer to FIG. 1) which converts the output signals into a series of time-sequenced digital intensity values $D_n$. Analog to digital converter 33 then provides the series of time-sequenced digital intensity values $D_n$ to a computer (either a micro-controller 34 or computer 37) where an earliest portion and a latest portion of time-sequenced digital intensity values $D_n$ are discarded. For example, suppose 200 intensity readings were taken. Then perhaps the first and last 25 would be discarded before an average intensity is determined using the remaining (undiscarded) portion of values. By discarding the first and last portions of the readings, only readings where gaming chip 500 is substantially in front of the light emitting devices and light detector will be utilized, thereby increasing the accuracy of the light readings.

Referring now to FIG. 4, there is illustrated a graph of reflected light intensity from a particular gaming chip 500. In the shown example, five different colors from five different light emitting devices $P_1$ through $P_n$ are utilized, however it may be appreciated that a lesser or greater number of different color light sources could also be employed. The intensity of the reflected light 30 is determined by the color content of gaming chip 500. For example, if gaming chip 500 were totally red, then the intensity of reflected light from the red light emitting devices 22 and 24 ($P_1$) will be very high, while the intensity of reflected light 30 from the other light emitting devices (green, blue, yellow, and bluegreen) will be very small since those colors would be absorbed by the red gaming chip 500. Actual gaming chips 500 contain a mixture of colors, which is different for each monetary denomination. Typically each monetary denomination has a different dominant color. Therefore, when a particular gaming chip 500 is sequentially illuminated by different color light sources, an intensity pattern similar to that of FIG. 4 will result. The different color lights (such as red, green, blue, yellow, and blue/green) occasion different intensities of reflected light 30. In the example of FIG. 4, the gaming chip 500 is predominantly blue, and has very little red. The light intensity is sensed by light detector 32, converted to a digital value in analog to digital converter 33, and then supplied to micro-controller 34. The various intensity levels will result in corresponding digital values $D_R$, $D_G$, $D_B$, $D_Y$, and $D_{B/G}$ respectively.

To ready system 20 for the recognition process, a particular denomination gaming chip 500, say $10, is passed in front of the different light sources and sequentially illuminated by each. Each illumination will result in a digital intensity value which is stored in memory 36. This process is repeated numerous times (in a preferred embodiment 100s or more times) in rapid succession in order to obtain an accurate average intensity level associated with each light source. This process is then repeated for each denomination (unique color) of gaming chip 500, therefore building a database of the pre-established intensity profiles corresponding to a plurality of different denomination gaming chips. Then, when an unknown gaming chip 500 is similarly passed in front of the light sources and illuminated, the measured digital intensity values are compared with the intensity profiles contained in memory 36 until a match is obtained, thereby recognizing the denomination (unique color) of the gaming chip 500 and providing an indication of the denomination. If no intensity profile match is found, then the gaming chip 500 is unauthorized and an appropriate message is generated.

Referring now to FIG. 5, to accomplish the automatic intensity adjustment, each pair of light emitting devices $P_1$ through $P_n$ is periodically energized when a gaming chip is not present. When detector circuit (position light emitting device 38 and light detector 32) detects the non-presence of a gaming chip, light emitting devices $P_1$ through $P_n$ are periodically and sequentially energized and their light of predetermined color having a first intensity strikes a calibration surface 42, the calibration surface 42 emitting reflected light 30 of a second intensity which is sensed by light detector 32. In a preferred embodiment, calibration surface is white thereby equally reflecting all colors, however other color calibration surfaces could also be utilized. The second intensity of light reflected from calibration surface 42 is digitized and compared with a pre-established baseline intensity level stored in memory 36. If the second intensity of reflected light 30 from calibration surface 42 is different from the pre-established baseline intensity level, the adjustment circuit 40, via digital potentiometer 44, adjusts the current and thus the first intensity level of light emitted from light emitting devices $P_1$ through $P_n$ so as to produce the pre-established second intensity level which matches the desired baseline level. In this manner, the system is continuously calibrated so that component aging and other factors do not affect the recognition of gaming chips 500.

FIG. 6 is a graph of showing the sequential and repeating energization of the light emitting devices. The red, green, blue, yellow, and blue-green light emitting devices are sequentially energized or turned ON for a period of approximately 15 microseconds. A dwell or OFF time of approximately 15 microseconds separates the periods of energization. For any one gaming chip 500, the cycle is repeated a 100 times or more in order to obtain an accurate average reading.

Figure 7:
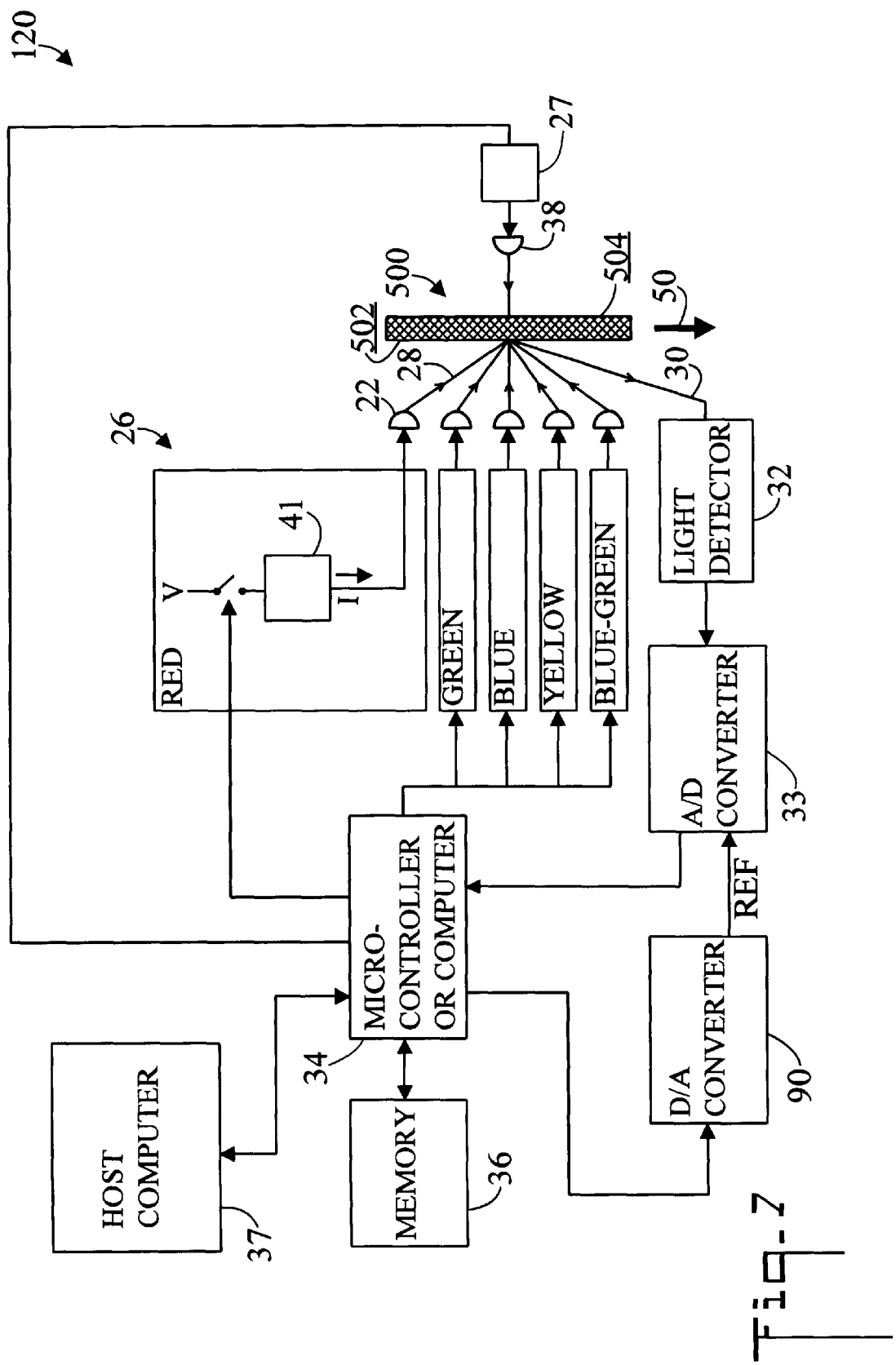

FIG. 7 is a block diagram of a second embodiment of the system for recognizing a gaming chip showing a different method of calibrating the light emitting devices, generally designated as 120. System 120 is similar to system 20, however system 120 does not include adjustment circuit 40 and digital potentiometer 44. Rather system 120 includes an adjustment potentiometer contained within constant current source 41 which allows current I to be changed. System 120 also includes a digital to analog (D/A) converter which is utilized to modify the measured second intensity level of reflected light.

System 120 operates as follows:
(1) each of the light emitting devices is energized and the second intensity level of reflected light from the calibration surface is measured,
(2) the current I supplied by constant current source 41 is then adjusted so that the second intensity level of reflected light equal a pre-established level. The pre-established level is a nominal or average level for the type of light emitting device being utilized.
(3) henceforth system 120 is operated in the manner previously described herein.
(4) as in system 20, when no gaming chip is present, each light emitting device is periodically energized and the second intensity level of reflected light is measured.
(5) micro-controller 34 then compares the measured second intensity level of reflected light with the previously determined pre-established level. The comparison between the measured second intensity level of reflected light and the pre-established level is sent to D/A converter 90 where it is converted to an analog reference which is used to modify the second intensity level of reflected light output form A/D converter 33.

For example, assume the current I through a light emitting device 22 was initially set to produce a second intensity level of reflected light of 10. As the system ages, the measured second intensity level from the calibration surface only measures 9. Micro-controller 34 computes the comparative ratio 10/9, sends that value to D/A converter 90, which in turn adjust the analog reference provided to A/D converter 33, which in turn modifies (increases by a factor of 10/9) the second intensity level of reflected light sent to micro-controller 34, thereby normalizing the light reading. It may be readily appreciated that the modification of the second intensity level of reflected light could also be accomplished in micro-controller utilizing software, thereby eliminating the need for D/A converter 90.

It is further noted that while in a preferred embodiments of systems 20 and 120, a pair or a plurality of pairs of light emitting devices are utilized, many of the principles of the present invention, such as constant current, calibration and calibration surface, multiple energizations, discarding a first and last portion of the multiple readings, etc., may also be practiced by simply using at least one light emitting device which emits light of a predetermined color.

The following parts have been found useful in implementing the present invention:

Micro-controller: Microchip PIC16C77
LEDs: Ledtronics P/N
   red-L200CWR3KF
   green-BP280CWAG6K-3.5VF-050T
   blue-BP280CWB1K-3, 3.6VF-050T
   yellow-L200CWY3KB
   blue-green-BP280CWBG2K-3, 3.5VF-050T
Light detector: Taos, or TI, P/N TSL252 (with integrated instrumentation amp)
Memory: National, 25LC160
Digital Potentiometer: Microchip MCP42010
Analog to Digital Converter: Part of Micro-controller: or, external National P/N ADC0820
Position light emitting device: L200CWY3KB
Digital to Analog Converter: National DAC 0808

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A system for recognizing a gaming chip, the gaming chip having a surface, said system comprising:
at least one light emitting device which when energized emits light of a predetermined color;

an energizing circuit for energizing said light emitting device;

a calibration surface;

when so energized, said light from said light emitting device striking said calibration surface, said calibration surface emitting reflected light;

a light detector for receiving said reflected light;

a detector circuit for detecting the presence or non-presence of a gaming chip; and, said energizing circuit periodically energizing said light emitting device when said detector detects said non-presence of a gaming chip.

2. A system for recognizing a gaming chip, the gaming chip having a surface, said system comprising:

at least one light emitting device which when energized emits light of a predetermined color;

an energizing circuit for energizing said light emitting device;

when so energized, said light from said light emitting device striking the surface of the gaming chip, the surface of the gaming chip emitting reflected light;

said light emitting device energized a plurality of times;

a light detector for receiving said reflected light;

each time said light detector receives said reflected light from said of light emitting device, said light detector providing an output signal proportional to an intensity of reflected light;

said output signals routed to an analog to digital converter which converts said output signals into a series of time-sequenced digital intensity values;

said analog to digital converter providing said series of time-sequenced digital intensity values to a computer wherein an earliest portion and a latest portion of said time-sequenced digital intensity values are discarded.

3. A method for recognizing a gaming chip having a surface, comprising:

providing a gaming chip, the gaming chip having a surface;

providing a plurality of pairs of light emitting devices, each said pair emitting light of a different color, an energizing circuit for energizing said pairs of light emitting devices, when so energized, said light from said pairs of light emitting devices striking the surface of the gaming chip, the surface of the gaming chip emitting reflected light, and a light detector for receiving said reflected light;

energizing said pairs of light emitting devices in rapid sequential order;

said light detector receiving and measuring said reflected light as each said pair of light emitting devices is energized;

comparing said reflected light from said pairs of energized light emitting devices with a plurality of pre-established intensity profiles, said plurality of pre-established intensity profiles corresponding to a plurality of different denomination gaming chips;

when said reflected light from said pairs of energized light emitting devices matches one of said plurality of pre-established intensity profiles, providing an indication of the denomination of the gaming chip;

energizing said pairs of light emitting devices a plurality of times, resulting in a corresponding plurality of time-sequenced reflected light intensity values;

discarding a first portion and a last portion of said plurality of time-sequenced intensity values; and, prior to said step of comparing, averaging a remaining portion of said plurality of time-sequenced intensity values.

4. The method according to claim 3, further including:

providing an adjustment circuit; and, said adjustment circuit automatically adjusting said first intensity level so as to produce a pre-established second intensity level.

* * * * *